(12) United States Patent
Harding et al.

(10) Patent No.: US 8,758,582 B2
(45) Date of Patent: Jun. 24, 2014

(54) ELECTROCHEMICAL TEST STRIP

(75) Inventors: Ian Harding, Somerville, MA (US);
Sridhar Iyengar, Salem, NH (US)

(73) Assignee: AgaMatrix, Inc., Salem, NH (US)

( * ) Notice: Subject to any disclaimer, the term of this patent is extended or adjusted under 35 U.S.C. 154(b) by 596 days.

(21) Appl. No.: 12/176,648

(22) Filed: Jul. 21, 2008

(65) Prior Publication Data

US 2009/0026091 A1    Jan. 29, 2009

Related U.S. Application Data

(60) Provisional application No. 60/951,264, filed on Jul. 23, 2007.

(51) Int. Cl.
*G01N 33/487* (2006.01)
*G01N 27/327* (2006.01)

(52) U.S. Cl.
CPC ................................. *G01N 27/3272* (2013.01)
USPC ............ 204/403.01; 204/403.02; 204/403.03; 204/403.04; 205/777.5; 205/781

(58) Field of Classification Search
CPC .................................................. G01N 27/3272
USPC .............. 204/403.01–403.15; 205/777.5–781
See application file for complete search history.

(56) References Cited

U.S. PATENT DOCUMENTS

| | | | |
|---|---|---|---|
| 4,897,173 A | 1/1990 | Nankai et al. |
| 4,999,582 A | 3/1991 | Parks et al. |
| 5,108,564 A | 4/1992 | Szuminsky et al. |
| 5,264,103 A | 11/1993 | Yoshioka et al. |
| 5,266,179 A | 11/1993 | Nankai et al. |
| 5,282,950 A | 2/1994 | Dietze et al. |
| 5,312,590 A | 5/1994 | Gunasingham |
| 5,410,059 A | 4/1995 | Fraser et al. |

(Continued)

FOREIGN PATENT DOCUMENTS

| | | | |
|---|---|---|---|
| EP | 0984069 A2 | | 3/2000 |
| EP | 1288654 A1 | | 3/2003 |
| EP | 1411348 A1 | | 4/2004 |
| WO | WO2007070093 | * | 6/2007 |

*Primary Examiner* — Bach Dinh
(74) *Attorney, Agent, or Firm* — Larson & Anderson, LLC (57) ABSTRACT

An electrochemical test strip is formed from a first insulating substrate layer, a second substrate layer, and an intervening insulating spacer layer. An opening in the insulating spacer layer defines a test cell which is in contact with the inner surface of the first substrate on one side and the inner surface of the second substrate on the other side. The size of the test cell is determined by the area of substrate exposed and the thickness of the spacer layer. Working and counter electrodes appropriate for the analyte to be detected are disposed on the first insulating substrate in a location within the test cell. The working and counter electrodes are associated with conductive leads that allow The second substrate is conductive at least in a region facing the working and counter electrodes. No functional connection of this conductive surface of the second substrate to the meter is required. When a potential difference is applied between the working and counter electrodes, because of the presence of the conductive surface on the second substrate, the relevant diffusion length is not dependent on the distance between working and counter electrodes, but is instead dependent on the distance between the first and second substrates (i.e., on the thickness of the spacer layer). This means that shorter measurement times can be achieved without having to reduce the spacing of the working and counter electrodes.

13 Claims, 8 Drawing Sheets

(56) References Cited

U.S. PATENT DOCUMENTS

| | | |
|---|---|---|
| 5,437,999 A | 8/1995 | Diebold et al. |
| 5,508,171 A | 4/1996 | Walling et al. |
| 5,589,326 A | 12/1996 | Deng et al. |
| 5,650,062 A | 7/1997 | Ikeda et al. |
| 5,700,695 A | 12/1997 | Yassinzadeh et al. |
| 5,708,247 A | 1/1998 | McAleer et al. |
| 5,710,011 A | 1/1998 | Forrow et al. |
| 5,846,702 A | 12/1998 | Deng et al. |
| 5,989,409 A | 11/1999 | Kurnik et al. |
| 6,059,946 A | 5/2000 | Yukawa et al. |
| 6,120,676 A | 9/2000 | Heller et al. |
| 6,258,229 B1 | 7/2001 | Winarta et al. |
| 6,262,264 B1 | 7/2001 | Buck, Jr. et al. |
| 6,284,125 B1 | 9/2001 | Hodges et al. |
| 6,484,046 B1 | 11/2002 | Say et al. |
| 6,618,819 B1 | 9/2003 | Adamovits et al. |
| 6,797,150 B2 * | 9/2004 | Kermani et al. ............ 205/777.5 |
| 6,942,770 B2 | 9/2005 | Cai et al. |
| 6,964,871 B2 | 11/2005 | Bell et al. |
| 7,022,218 B2 * | 4/2006 | Taniike et al. ............. 205/777.5 |
| 2003/0098233 A1 | 5/2003 | Kermani et al. |
| 2003/0116447 A1 * | 6/2003 | Surridge et al. ............ 205/777.5 |
| 2004/0005721 A1 * | 1/2004 | Tanike et al. .................. 436/518 |
| 2004/0043477 A1 * | 3/2004 | Schibli ....................... 435/287.1 |
| 2004/0225330 A1 | 11/2004 | Kramer et al. |
| 2005/0109637 A1 | 5/2005 | Iyengar et al. |
| 2005/0252769 A1 | 11/2005 | Cho |
| 2005/0258036 A1 | 11/2005 | Harding |
| 2006/0091006 A1 * | 5/2006 | Wang et al. .............. 204/403.02 |
| 2006/0151323 A1 * | 7/2006 | Cho ........................ 204/403.04 |
| 2006/0169599 A1 | 8/2006 | Feldman et al. |

\* cited by examiner

ELECTROCHEMICAL TEST STRIP

STATEMENT OF RELATED APPLICATIONS

This application claims the benefit under 35 USC §119 of U.S. Provisional Application Ser. No. 60/951,264, filed Jul. 23, 2007, which application is incorporated herein by reference in its entirety.

BACKGROUND OF THE INVENTION

This application relates to a design for small volume electrochemical test strips suitable for amperometric determination of analytes in a liquid test sample. Disposable, single-use electrochemical test strips are commonly employed in the determination of analytes, particularly by diabetes in the determination of blood glucose levels. Advancements in design of these strips have frequently focused on the ability to use smaller samples, since smaller blood samples can be obtained with less pain. Examples of such test strips can be seen, for example for U.S. Pat. Nos. 5,437,999, 5,650,062, 5,700,695, 6,484,046, and 6,942,770 and Applications Nos. US2004/0225230, and US2006/0169599A1.

Figure 1A:
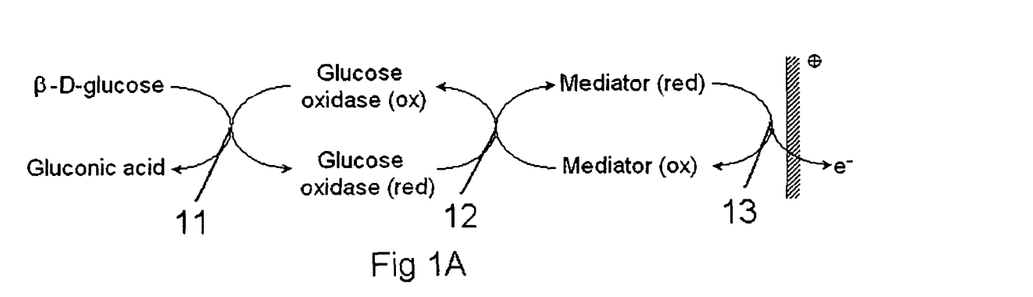
FIGS. 1A and B show reactions from a glucose detector.
Figure 1B:
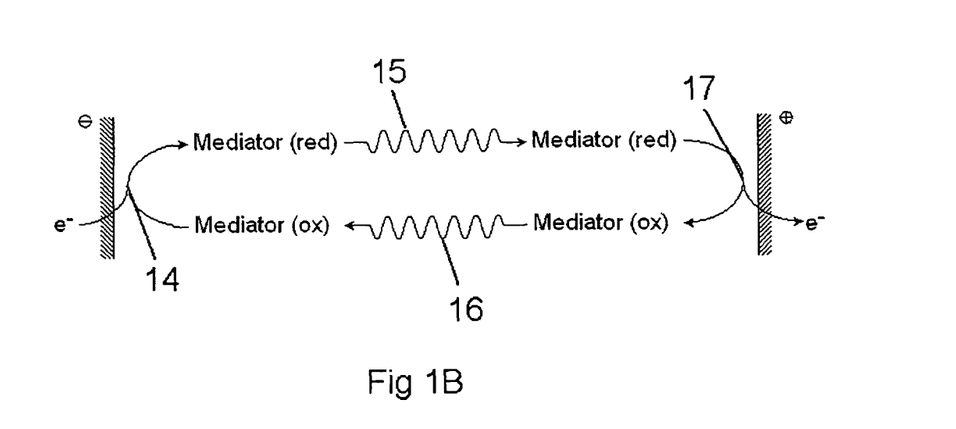

In known electrochemical sensors for determination of glucose the reactions depicted in FIGS. 1A and 1B may be used. Glucose present in the sample is oxidized in reaction 11 by an enzyme, such as glucose oxidase to form gluconic acid (or gluconolactone) and reduced enzyme. The reduced enzyme is regenerated to its active oxidized form by interaction 12 with oxidized mediator, for example ferricyanide. When there is an appropriate potential difference between the working and counter electrodes, the resulting reduced mediator is converted 13 to oxidized mediator at the working electrode, with concurrent oxidation of reduced mediator at the counter electrode 14. In addition the reduced mediator may diffuse 15 from the counter electrode and when it reaches the working electrode it can be converted 17 to oxidized mediator and diffuse 16 to the counter electrode complete the cycle.

Figure 2:
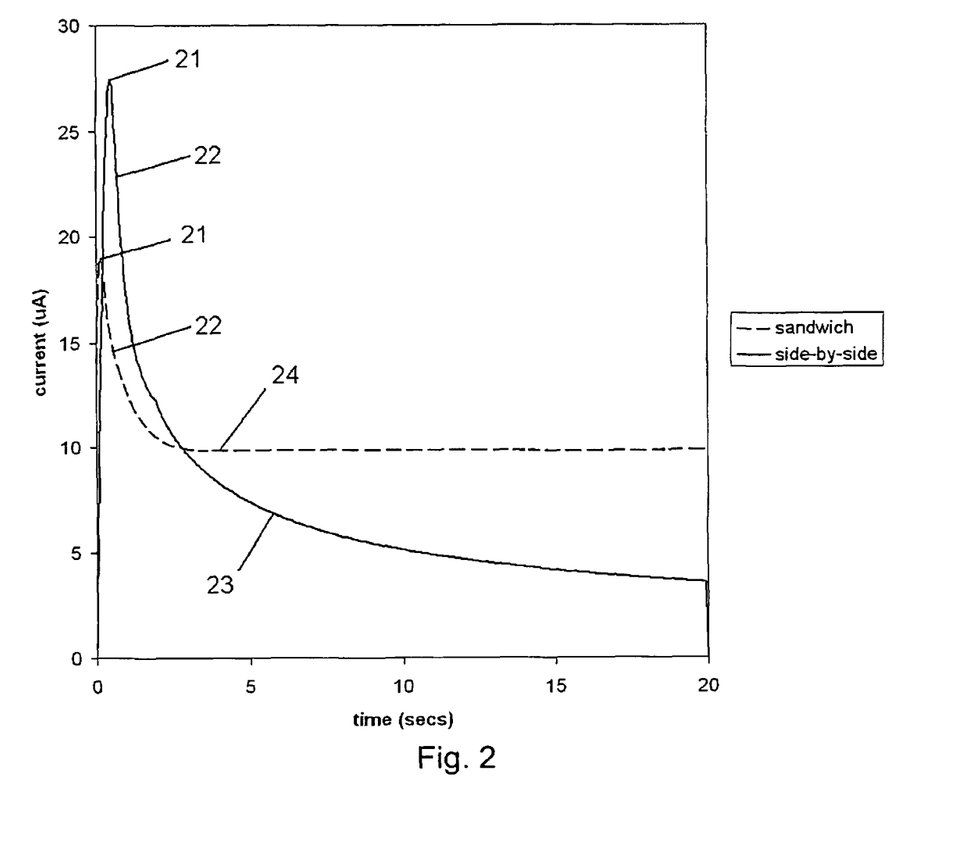
FIG. 2 shows a schematic of two exemplary current traces as a function of time in accordance with the prior art.

FIG. 2 shows two exemplary current traces in sample cells according to the prior art, in which the working and counter electrodes are disposed in a closely spaced facing (sandwich) arrangement (dotted line) and a more openly spaced side-by-side arrangement (solid line). The mediator is freely diffusible between the two electrodes in both cases. The x-axis (time) starts when the measurement potential is supplied. An initial current spike 21 is observed in both traces that results from the charging of the double layer on, and consuming the mediator 13 close to, the portion of the electrode surface covered at the time of the measurement potential is first applied. Thereafter, there is a decline in current 22 because of the smaller flux of mediator arriving at the working electrode, resulting from the depletion of mediator in the vicinity of the electrode. In the solid trace this persists to longer times and lower currents 23 because of continued depletion of the mediator. In the dotted line a limiting current 24 is reached, which is caused by a stable flux of reduced mediator being generated at the nearby counter electrode 14 and diffusing 15 to the working electrode. This is balanced by a flux 16 of oxidized mediator going the other way.

Determination of the analyte concentration in solution can be made at various points along the current traces. When the electrodes are in a closely spaced facing arrangement this includes at the peak value 21, the plateau level 24, or during the decrease 22 in between; the plateau current 24 has a simple linear relationship with analyte concentration and the estimate of the current can be improved by averaging data in this region over a time period. When the electrodes are side-by-side the analyte concentration can be determined from the data at the peak value 21 or in the decrease 22, 24.

Figure 3:
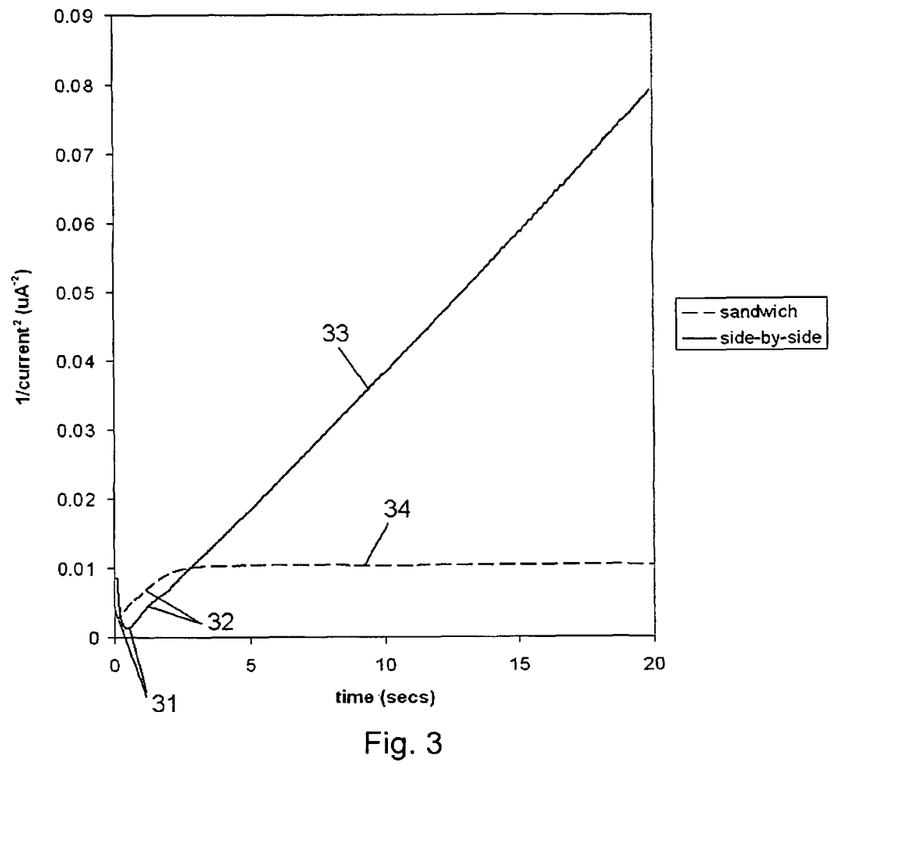
FIG. 3 shows a schematic of two exemplary current traces presented as the inverse square of current as a function of time in accordance with the prior art.

To use data from the decrease 22, 24 it is possible to recalculate the current data as the inverse square of current. The results of such a calculation on the data from both traces of FIG. 2 are shown in FIG. 3, with the minimna 31 corresponding to the peaks 21, the initial straight slopes 32 corresponding to the curved decline in current 22, and the continuation of the curving decline 23 being a continuation 33 of the initial straight slope 32 for the side-by-side geometry. The plateau for the sandwich geometry 24 also manifests as a plateau 34.

The results with the sandwich geometry of FIGS. 2 and 3 require a sample cell with electrodes that are sufficiently close that flux of reduced mediator 15 being generated 14 at the counter electrode arrives rapidly and stabilizes rapidly at the working electrode 13 during the course of data collection. The transition between the working electrode being unaffected by the counter electrode and being in a steady state with the flux from the counter electrode produces the curve between the straight parts 32 and 34 in FIG. 3. To minimize the time required for the test, it is desirable to decrease the time required for diffusion to occur, and for a steady state current to be established. Commonly assigned US Patent Publication No. 2005/0258036, which is incorporated herein by reference discloses an approach to this problem, adapted for use in the context of facing electrodes. The electrodes are in close proximity, which allows the system to reach the stable plateau quickly. This favours small sample chambers and hence small sample sizes.

However, this approach is not well-suited to electrodes disposed on the same substrate, i.e., to side-by-side electrodes. The results with the side-by-side geometry of FIGS. 2 and 3 require a sample cell that is sufficiently large that flux of reduced mediator being generated at the counter electrode 14 does not arrive at the working electrode during the course of measurement. This favours large sample chambers and hence large sample sizes. Decreased sample sizes can be achieved simply by placing the electrodes closer together, but placing the electrodes closer together means flux 15 from the counter electrode arrives at the working electrode and generates an additional signal 17, causing the region 33 to bend, reducing the accuracy of the estimate of concentration from the slope. However, the side-by side geometry means that a steady state will not be set up as rapidly as in the sandwich geometry and so the bending will last a long time before reaching a stable plateau where more reliable data will be available to estimate the analyte concentration.

The present invention provides a simple approach to decreasing the time required to arrive at a steady state current for an electrochemical test strip with side-by-side electrodes and increasing the accuracy of the estimated concentration of the analyte that can be achieved without increasing the complexity of the manufacturing process.

SUMMARY OF THE INVENTION

The present invention provides an electrochemical test strip comprising a first insulating substrate layer, a second substrate layer, and an intervening insulating spacer layer. An opening in the insulating spacer layer defines a test cell which is in contact with the inner surface of the first substrate on one side and the inner surface of the second substrate on the other side. The size of the test cell is determined by the area of substrate exposed and the thickness of the spacer layer.

Working and counter electrodes appropriate for the analyte to be detected are disposed on the first insulating substrate in a location within the test cell. The working and counter electrodes are associated with conductive leads that allow connection of the electrodes to a meter for determination of analyte. At least the inner surface of the second substrate is conductive, at least in a region facing the working and counter electrodes. No functional connection of this conductive surface of the second substrate to the meter is required.

In use, a potential difference is applied between the working and counter electrodes. Because of the presence of the conductive surface on the second substrate, the relevant diffusion length is not dependent on the distance between working and counter electrodes, but is instead dependent on the distance between the first and second substrates (i.e., on the thickness of the spacer layer). This means that shorter measurement times can be achieved without having to reduce the spacing of the working and counter electrodes.

DETAILED DESCRIPTION OF THE INVENTION

This application relates to electrochemical test strips. In the detailed description that follows, the invention will be discussed primarily in the context determination of blood glucose levels. This use of one primary detection system, however, should not be taken as limiting the scope of the invention, as the invention can be used in the detection of any analyte that can be detected using an electrochemical test strip.

Definitions

In the specification and claims of this application, the following definitions are relevant. Numerical values in the specification and claims of this application should be understood to include numerical values which are the same when reduced to the same number of significant figures and numerical values which differ from the stated value by less than the experimental error of conventional measurement technique of the type described in the present application to determine the value.

The term "analyte" as used in the specification and claims of this application means a component of a sample to be measured. The analyte may be one that is directly oxidized or reduced in the electrochemical test strip, or one that is oxidized or reduced through the use of an enzyme and/or a redox mediator. Non-limiting examples of specific analytes include glucose, hemoglobin, cholesterol and vitamin C.

The term "redox mediator" as used in the specification and claims of this application means a chemical species, other than the analyte, that is oxidized and/or reduced in the course of a multi-step process transferring electrons to or from the analyte to an electrode of the electrochemical cell. Non-limiting examples of mediators include ferricyanide, p-benzoquinone, phenazine methosulfate, methylene blue, ferrocene derivatives, osmium mediators, for example as described in U.S. Pat. Nos. 5,589,326; 5,710,011, 5,846,702 and 6,262,264, which are incorporated herein by reference, ruthenium mediators, such as ruthenium amines, and ruthenium complexes as described in U.S. Pat. No. 5,410,059.

The term "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

The term "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

The term "side-by-side electrodes" refers to a pair of electrodes disposed on a common substrate surface. The electrodes may be parallel strips, concentric or nested rings, nested spirals or any other suitable spatial arrangement.

The term "sandwich geometry electrodes" refers to a pair of electrodes disposed in a closely spaced facing arrangement with space for the sample in between.

Prior Art Strips

Figure 4A:
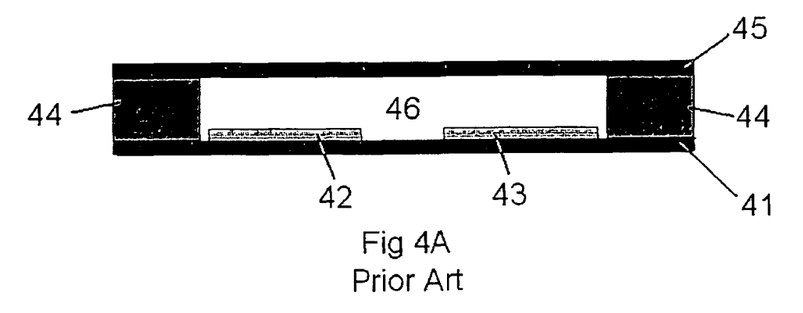
FIGS. 4A and 4B show a cross section of a test strip in accordance with the prior art, and the relevant diffusion paths in such as test strip.

FIG. 4A shows a cross section through the test cell of a test strip according to the prior art. The strip has a first insulating substrate 41 on which are disposed working electrode 42 and counter electrode 43. Insulating spacer layer 44 separates the first insulating substrate 41 from the second insulating substrate 45. An opening in the spacer layer 44 defines two dimensions of the test cell 46, while the thickness of the spacer layer 44 defines the third.

Figure 4B:
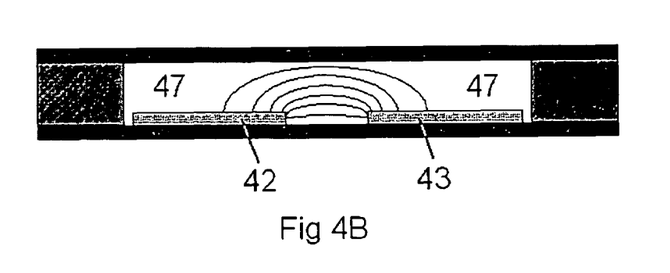

In the amperometric determination of an analyte a potential difference is applied between electrodes 42 and 43. For example, in the determination of glucose as described above, the working electrode 42 is suitably fixed at a potential of +300 mV relative to the counter electrode. The situation when flux from the counter electrode 15 arrives at the working electrode and is oxidized 17 has been discussed in terms of the increase in the electrochemical current, where the region 33 is caused to bend, reducing the accuracy of the estimate of concentration from the slope. Diffusion of mediator 15, 16 occurs between the electrodes along the lines shown in FIG. 4B. Thus, the time necessary for diffusion to start affecting the slope of the region 32, 33, is dependent upon the spacing between electrodes 42 and 43. However, the side-by side geometry means that a steady state will not be set up as rapidly as in the sandwich geometry because there is a large portion of the volume 47 where mediator will have to diffuse a long distance before reaching equilibrium with the two electrodes. Only once this steady state is reached will the data reach a simple plateau like 24, 34 where more reliable data will be available to estimate the analyte concentration.

The large portion of the volume 47 that is remote from the main flux between the electrodes will affect the testing time, sample volume and accuracy of the system. To avoid the inaccuracy of deviations (bending) in the region 33 the sample must be sufficiently large that all data is collected before any flux from the counter electrode affects data collection at the working electrode. For smaller sample sizes the reduced time before this occurs limits the amount of linear data 32 that can be collected and hence the accuracy of the concentration estimate that can be made from it. Steady-state data will only be available after the entire region 47 has been brought into steady state and the side-by-side geometry is not efficient at doing this. The bending will therefore last a long time before reaching a stable plateau, giving an extended test time. In addition, the accuracy of the concentration estimate will be sensitive to the distance between the electrodes and for the side-by-side geometry this will be defined by the repeatability of separation of the adjacent edges of the two electrodes in the disposable test strip. This is likely to introduce significant errors.

Test Strips of the Invention

Figure 5A:
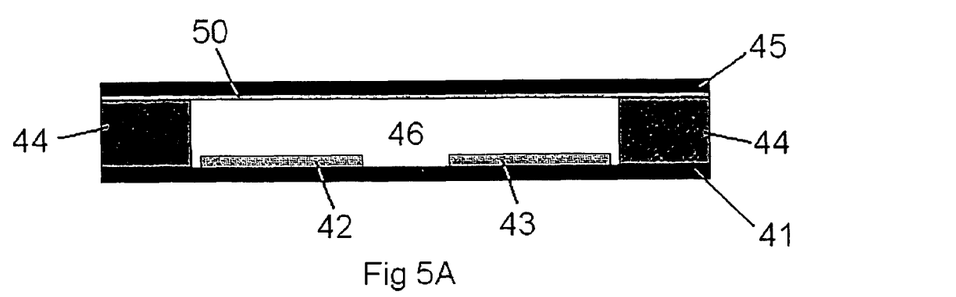
FIGS. 5A and 5B show a cross section of a test strip in accordance with the invention, and the relevant diffusion paths in such as test strip.

FIG. 5A shows a cross section through the test cell of an embodiment of a test strip according to the invention. The strip has a first insulating substrate 41 on which are disposed working electrode 42 and counter electrode 43. Insulating spacer layer 44 separates the first insulating substrate 41 from the second insulating substrate 45. However, insulating substrate 45 has a conductive coating 50 on its inner surface. An opening in the spacer layer 44 defines two dimensions of the test cell 46, while the thickness of the spacer layer 44 defines the third. The conductive coating 50 is exposed in the test cell 46 and faces the working and counter electrodes 42, 43.

Figure 5B:
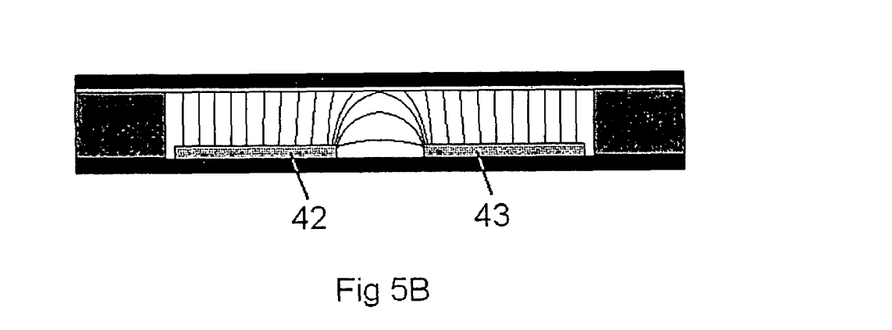

In the amperometric determination of an analyte using the test strip depicted in FIG. 5A, a potential difference is applied between electrodes 42 and 43. For example, in the determination of glucose as described above, the working electrode 42 is suitably fixed at a potential of +300 mV relative to the counter electrode. Diffusion of mediator 15, 16 of course occurs between the electrodes as shown in FIG. 1B. However, because of the presence of the conductive coating 50, this diffusion is not a limiting factor in the time required to established a steady state current. Rather, the relevant limiting diffusion is that extending from the electrodes 42, 43 to the facing surface of the conductive coating 50 as shown by the lines in FIG. 5B. Thus, the time necessary for diffusion is dependent upon the thickness of the spacer layer 44.

Figure 6:
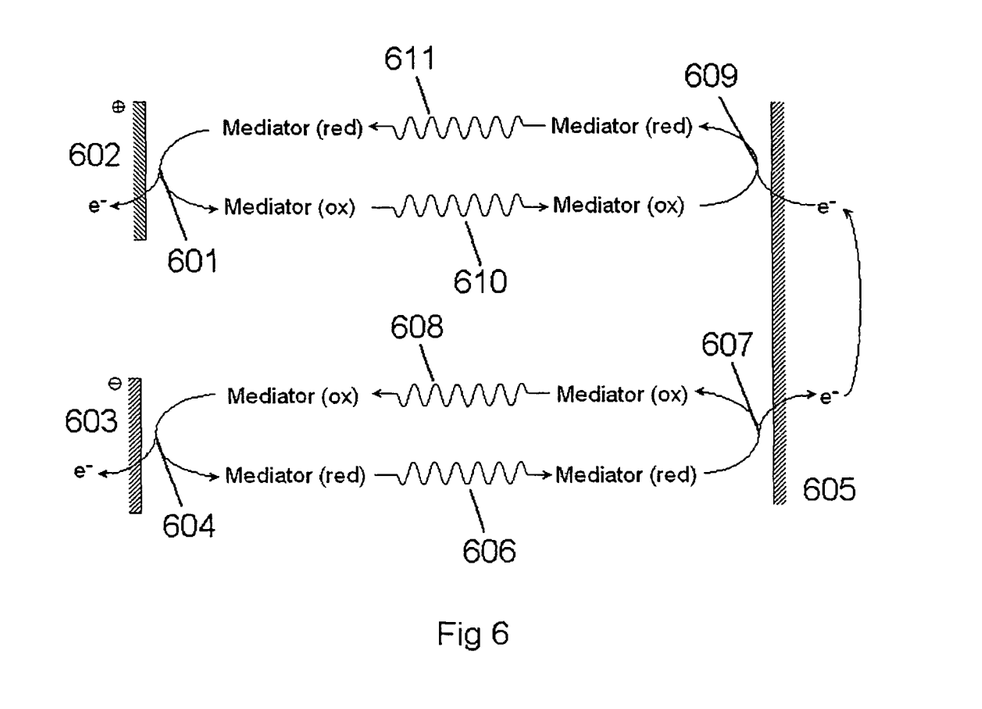
FIG. 6 shows the reactions relevant to determination of analyte concentration in a test strip in accordance with the invention.

This change in the relevant portions of the diffusion occurs because the conductive coating 40 short circuits the test cell. The relevant reactions are shown in FIG. 6 where reduced mediator is oxidized 601 at the working electrode 602 and the electron transfer out of solution is balanced at the working electrode 603 by reduction of the oxidized mediator 604. Rather than diffusing directly between the electrodes as in 15, 16 much of the mediator flux is transformed at the conductive layer 605: the flux of reduced mediator from the counter electrode 606 can give up electrons 607 into conductive layer 605 and diffuse back to the counter electrode 608 in the oxidized form without ever reaching the working electrode. The electrons transferred 607 into the conductive layer 605 must be balanced by electrons transferred 609 out of the conductive layer onto oxidized mediator where they are in abundance. An abundant supply of oxidized mediator is found in the flux of oxidized mediator 610 produced by the working electrode reaction 601. The overall transfer of reduced mediator from the counter electrode 603 to the working electrode 602 is completed by diffusion of reduced mediator 611 from the conductive layer 605 to the working electrode 602.

The reactions 607, 609 shown in FIG. 6 involve simultaneous electron transfer into and out of the conductive layer 605. This is possible, in fact it is a requirement, because the conductive layer 605 acts as an electrode and the chemical potential of a solution in contact with an electrode will always try to reach equilibrium with the electrode potential. Since the layer 605 is conductive, it can only be at a single uniform potential throughout, so it is the chemical potentials of the various parts of the solution in contact with the conductive later 605 that are brought into equilibrium through electron transfer. This electron transfer is effectively instantaneous in the conductive layer 605 so it provides a very rapid path for electron transfer from regions of the test cell that would otherwise take much time to reach a steady state. In addition, the proximity of the conductive layer to the electrodes and their parallel orientation render much of the diffusion effectively one-dimensional.

The simple addition of a conductive layer over side-by-side electrodes therefore rapidly reduces the time it takes to generate a steady-state flux between the electrodes. This allows much smaller sample sizes, since flux between the electrodes is no longer undesired. It allows an improved accuracy because the flux is now arriving principally at the electrode surfaces rather than along their adjacent edges and so is dependent on the far more controllable electrode area than the electrode separation. It also produces a near one-dimensional diffusion at a rapidly reached steady state and so the ability to probe the system by electrochemical techniques and apply useful corrections such as those described in US Patent Publication No. US2005/0109637A1, and U.S. Pat. No. 6,284, 125 are at their most effective.

Figure 7:
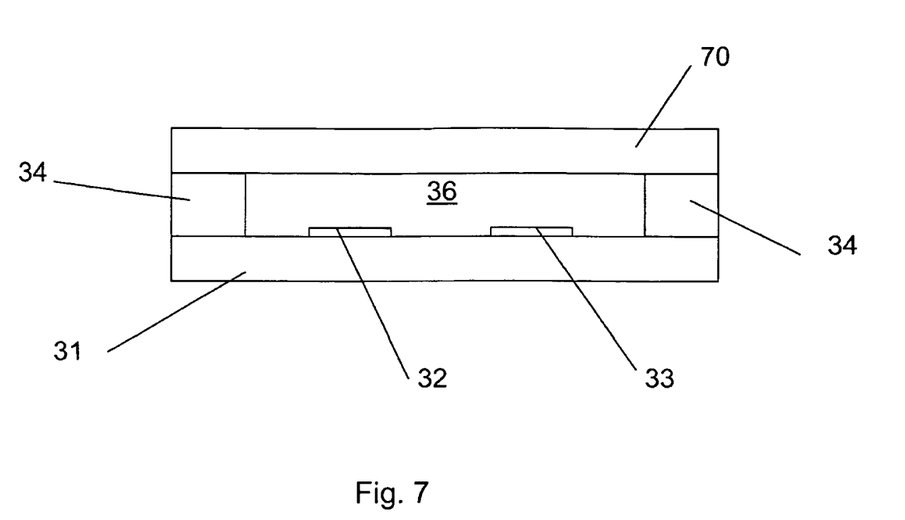
FIG. 7 shows a cross section through the test cell of an embodiment of a test strip according to the invention.

FIG. 7 shows a cross section through the test cell of an embodiment of a test strip according to the invention. In FIG. 7, the second insulating layer 35 and the conductive coating 40 are replaced with a conductive layer 70.

Figure 8:
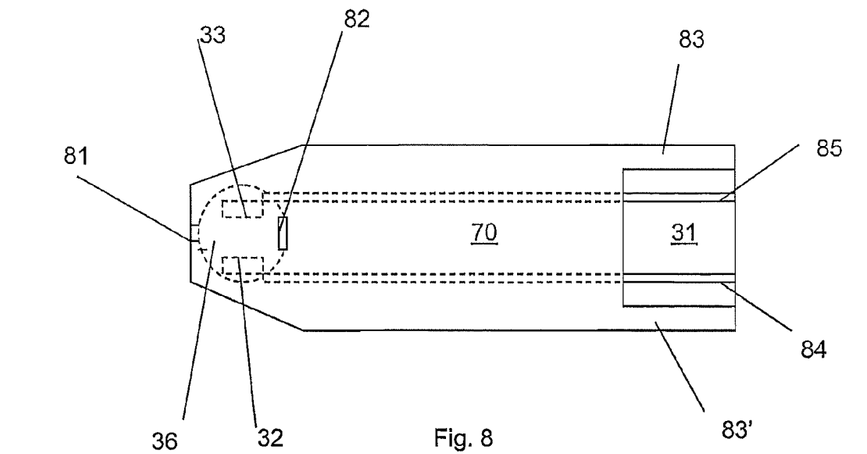
FIG. 8 shows a top view of a test strip in accordance with the invention.

FIG. 8 shows a top view of a test strip of the type shown in FIG. 8. Test cell 36 is opened to the exterior to permit introduction of sample via channel 61 formed in the spacer layer. A vent 82 is formed through the conductive layer 70 (or alternatively through the insulating substrate 31 to facilitate flow into the test cell. Working and counter electrodes 32, 33 are connected to conductive leads 84, 85, respectively. At the end opposite the channel 81, a portion of the conductive layer 60 and the spacer layer are cut away to expose a part of the insulating substrate 31 and of leads 84 and 85 to allow connection of these leads with a meter. In the embodiment shown in FIG. 8, part 83, 83' of the conductive layer 60 is left in place at the edges of the test strip. This not only provides better dimensional stability but electrical contact with this layer can be used to detect insertion of a test strip into a test meter, for example as described in U.S. Pat. Nos. 4,999,582, 5,282,950 and 6,618,819, which are incorporated herein by reference. The electrical contact could be between two points on either one of the parts 83, and 83' or it could be between one point on part 83 and another part on part 83'.

The embodiment disclosed in FIG. 8 can also facilitate detection of sample introduction into the cell. For example, by monitoring for a change in resistance between the conductive layer 80 and either of the working or counter electrodes 32, 33, the introduction of sample into the test cell can be monitored, and used as a signal to activate application of a measurement potential. The use of sample detection in this way is known in the art, for example from U.S. Pat. Nos. 5,108,564 and 5,266,179, which ate incorporated herein by reference.

While the embodiment of FIG. 8 is convenient for use in insertion and sample detection, embodiments with an insulating outer surface can also be used providing that a portion of the insulation is removed or a lead is formed to allow contact with the conductive surface. It should be understood, however, that no electrical signal needs to be applied to or measured from this conductive coating or layer in order to achieve the benefits of reduced testing time.

Figure 9:
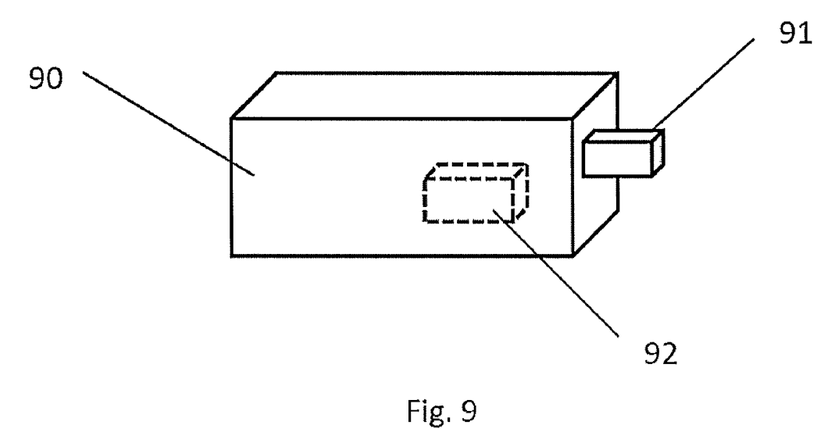
FIG. 9 shows a combination of a test strip and a meter.

FIG. 9 shows a combination of a meter 90 and a test strip 91 inserted into the meter. The meter includes electronic circuitry 92 for applying potential to the working and counter electrodes, analyzing signals and displaying a result. (connection to the test strip not shown) The electronic circuitry 92 evaluates the current between the working and counter electrodes for determination of analyte. No functional connection between the meter and the conductive region of the second substrate is required for determination of analyte.

The invention claimed is:

1. A method for detecting an analyte in a sample comprising the steps of:
   introducing the sample into a test cell of an electrochemical test strip for detection of the analyte comprising:
      a first insulating substrate layer,
      a second substrate layer, and
      an intervening insulating spacer layer, wherein
         (a) an opening in the insulating spacer layer defines the test cell which is in contact with the inner surface of the first substrate on one side and the inner surface of the second substrate on the other side; and
         (b) the size of the test cell is determined by the area of the first and second substrates exposed and the thickness of the spacer layer;
   working and counter electrodes appropriate for the analyte to be detected disposed on the first insulating substrate in a location within the test cell, said working and counter electrodes being associated with conductive leads that allow connection of the electrodes to a meter for determination of analyte;
   wherein a region of the second substrate facing the working and counter electrodes is conductive and has no connector for connection with a meter for determination of analyte;
   wherein a redox mediator is disposed in the test cell;
   applying a potential between the working and counter electrodes, but not to the conductive region of the second substrate, thereby reducing an oxidized form of the redox mediator at the counter electrode and oxidizing a reduced form of the redox mediator at the working electrode, thereby generating a current indicative of analyte in the sample;
   wherein the overall transfer of electrons from the counter electrode to the working electrode is accomplished by diffusion of reduced mediator from the counter electrode to the conductive region of the second substrate and then diffusion of reduced mediator from the conductive region of the second substrate to the working electrode, and
   measuring the current to obtain a determination of analyte in the sample.

2. The method of claim 1, wherein the working electrode comprises an enzyme and the redox mediator.

3. The method of claim 2, wherein the analyte is glucose and the enzyme is glucose oxidase or glucose reductase.

4. The method of claim 3, wherein the entirety of the second substrate layer is conductive.

5. The method of claim 4, wherein the working electrode comprises an enzyme and the redox mediator.

6. The method of claim 5, wherein the analyte is glucose and the enzyme is glucose oxidase or glucose reductase.

7. The method of claim 4, further comprising the step of monitoring the resistance between the conductive second substrate layer and the working and/or counter electrodes as a measure of filling of the test cell with sample.

8. The method of claim 7, wherein the working electrode comprises an enzyme and the redox mediator.

9. The method of claim 8, wherein the analyte is glucose and the enzyme is glucose oxidase or glucose reductase.

10. The method of claim 1, wherein the second substrate layer comprises a second insulating substrate and a conductive coating.

11. The method of claim 10, wherein the working electrode comprises an enzyme and the redox mediator.

12. The method of claim 11, wherein the enzyme is glucose oxidase or glucose reductase.

13. The method of claim 1, wherein the working electrode is a single strip of conductive material and the counter electrode is a single strip of conductive material, wherein the working and counter electrodes are in side-by-side parallel arrangement in the test cell.

* * * * *